(12) United States Patent
Nakanishi (10) Patent No.: US 7,564,937 B2
(45) Date of Patent: Jul. 21, 2009

(54) X-RAY CT DEVICE AND METHOD OF CONTROLLING THE SAME

(75) Inventor: Satoru Nakanishi, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/038,205

(22) Filed: Feb. 27, 2008

(65) Prior Publication Data
US 2008/0205587 A1 Aug. 28, 2008

(30) Foreign Application Priority Data
Feb. 28, 2007 (JP) ............... 2007-050700

(51) Int. Cl.
*A61B 6/00* (2006.01)
(52) U.S. Cl. .......................... 378/4; 378/901
(58) Field of Classification Search ............... 378/4–20, 378/91, 98, 98.2, 98.8, 114–116, 901
See application file for complete search history.

(56) References Cited

U.S. PATENT DOCUMENTS 5,170,439 A 12/1992 Zeng et al.
5,784,481 A * 7/1998 Hu .............................. 382/131
6,584,166 B2 6/2003 Taguchi
7,197,105 B2 * 3/2007 Katsevich ....................... 378/4

FOREIGN PATENT DOCUMENTS

JP 5-324801 12/1993
JP 2002-360562 12/2002

OTHER PUBLICATIONS

U.S. Appl. No. 12/038,205, filed Feb. 27, 2008, Nakanishi.
U.S. Appl. No. 12/169,963, filed Jul. 9, 2008, Nakanishi, et al.

* cited by examiner

*Primary Examiner*—Jurie Yun
(74) *Attorney, Agent, or Firm*—Oblon, Spivak, McClelland, Maier & Neustadt, P.C.

(57) ABSTRACT

An X-ray CT device generates an X-ray beam in the shape of a cone along the body axis of a subject from an X-ray tube to the subject and detects the X-rays that pass the subject by a two-dimensional detection system during a linear track scan. In addition, the X-ray CT device detects X-rays from a relative rotation movement of the X-ray tube and the subject during the linear track scan under the same condition. A reconstruction device reconstructs an image by back projection of the data of the subject based on the X-rays detected in the two scans.

8 Claims, 8 Drawing Sheets

| edge FOV | Shape of reconstruction ROI |
|---|---|
| c FOV | Rectangle ROI |
| Bpj Min Mask Fov | Octagon ROI |
| 0 | Hexagon ROI |

| FOV | Line Scan Length [mm] | |
|---|---|---|
| | With extrapolation mask | Without extrapolation mask |
| SS(180mm) | 512.00 | 534.59 |
| S(240mm) | 512.00 | 544.00 |
| M(320mm) | 512.00 | 558.55 |
| L(400mm) | 512.00 | 576.00 |
| LL(500mm) | 512.00 | 603.43 |

| Data No. | C1 | C2 | C3 | C4 | C5 | C6 | C7 | C8 |
|---|---|---|---|---|---|---|---|---|
| Tube voltage (kV) | 120 | 120 | 120 | 120 | 120 | 80 | 120 | 120 |

FIG. 12

| Patient $A_{1A}$ | $L_A$ | $C_A$ |
|---|---|---|
| Patient B | $L_B$ | $C_B$ |
| ⋮ | ⋮ | ⋮ |
| Patient $A_{2A}$ | $L_{A'}$ | $C_{A'}$ |

X-RAY CT DEVICE AND METHOD OF CONTROLLING THE SAME

CROSS-REFERENCE TO RELATED APPLICATIONS

This application is based upon and claims the benefit of priority from prior Japanese Patent Application No. 2007-050700, filed Feb. 28, 2007, the entire contents of which are incorporated herein by reference.

BACKGROUND OF THE INVENTION

1. Field of the Invention

The present invention relates to an X-ray CT device that realizes cone-beam reconstruction, as well as a method of controlling the device. The present invention relates particularly to a medical X-ray CT device for radiating a living body with X-rays and thereby acquiring internal body information as an image.

2. Description of the Related Art

In the field of X-ray CT devices, the third-generation CT is defined as a system of collecting projection data from various angles as its X-ray tube for producing an X-ray beam and X-ray detector positioned across a subject from the X-ray tube rotate around the subject. The conventional technologies adopt an X-ray beam of a fan shape and a detector of a one-dimensional array type.

Scan systems can be divided into two types, conventional scan and helical scan. In the conventional scan, the X-ray tube moves around on a certain circular track. On the other hand, the helical scan is defined as the X-ray source and the detector continuously rotating around a subject while a bed carrying the subject moves along the body axis in synchronization with the rotation of the X-ray source and the detector. The helical scan has been given this name because the X-ray tube moves on a helical track when the coordinates of the tube moving along with the subject are considered. The distance between the changed positions of the X-ray tube along the body axis, in other words z-axially, after one rotation is defined as the helical pitch.

In addition, a CT incorporating a detector of a two-dimensional array type has been known as a third- or fourth-generation CT. This CT is provided with an X-ray tube that generates a conical X-ray beam spreading along the body axis, unlike fan-shaped X-rays, and an X-ray detector that is formed by attaching, for example, N rows of one-dimensional array detectors together z-axially so as to arrange detection elements in a matrix. Such a device is called a cone-beam CT scanner.

Among tomographic technologies employing conventional scan systems, a circular cone-beam reconstruction suggested by Feldkamp et al. is known for the reconstruction of an image obtained by the tomography (see Jpn. Pat. Appln. KOKAI Publication No. 2002-360562, for example). It has been shown, however, that the circular cone-beam reconstruction method produces cone-beam artifacts, which hampers production of complete data and degrades the image quality.

Solutions to this problem includes a line-and-circle (hereinafter referred to as line-circle) reconstruction technique, which employs line scan in addition to circular scan, as described in Jpn. Pat. Appln. KOKAI Publication No. 5-324801. Katsevich suggests line-circle reconstruction that adopts a filtered back projection system.

There is a drawback, however, in implementing such line-circle reconstruction on a system.

That is, additional scan is required to obtain line data. This is regarded as extra exposure to radiation, and the amount of exposure should be reduced as much as possible. Furthermore, the condition of collecting line data needs to match the condition of collecting circle data. If it does not match, artifacts may not be reduced. In addition, when the reconstruction is retried, preferable results cannot be attained unless the reconstruction is executed with suitable data combination.

BRIEF SUMMARY OF THE INVENTION

The purpose of the present invention is to provide an X-ray CT device and a method of controlling the device, with which the amount of additional radiation exposure can be minimized by devising a method of obtaining line data and the like, and with which reconstruction is prevented from incorporating erroneous data.

In particular, the present invention offers:

an X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the X-ray CT device comprising:

a scan controlling unit for performing control in such a manner that first projection data is acquired by moving the X-ray source and the patient in a relative manner to each other along the body axis of the patient and second projection data is acquired by rotating the X-ray source around the patient;

a reconstruction processing unit for performing a reconstruction process by combining the first projection data and the second projection data; and a determining unit for determining whether a scan should be performed or whether the reconstruction process should be performed, based on a scan condition of the first projection data and a scan condition of the second projection data.

The present invention also offers:

an X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the X-ray CT device comprising:

a first scan controlling unit for performing control in such a manner that first projection data is acquired by moving the X-ray source and the patient in a relative manner to each other along the body axis of the patient;

a range setting-up unit for displaying a scan range set-up image that is used to set up a scan range or an image producing range, based on the first projection data;

a second scan controlling unit for performing control in such a manner that second projection data is acquired by rotating the X-ray source around the patient in accordance with the scan range or the image producing range set up by the range setting-up unit; and a reconstruction processing unit for performing a reconstruction process by combining the first projection data and the second projection data.

Furthermore, the present invention offers:

a method of controlling an X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the method comprising steps of:

acquiring first projection data by moving the X-ray source and the patient in a relative manner to each other along the body axis of the patient;

displaying a range set-up image that is used to set up a scan range or an image producing range, based on the first projection data and thereby setting up the scan range or the image producing range;

acquiring second projection data by rotating the X-ray source around the patient in accordance with the scan range or the image producing range set up by the range setting-up unit; and performing a reconstruction process by combining the first projection data and the second projection data.

The present invention offers:

an X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the X-ray CT device comprising:

a reconstruction processing unit for reconstructing an image based on first projection data acquired by moving the X-ray source and the patient in a relative manner to each other along the body axis of the patient and second projection data acquired by rotating the X-ray source around the patient; and a controlling unit configured to select a first mode in which a scan range or an image producing range is set up based on the first projection data and a second mode in which the first projection data and the second projection data is acquired after acquiring a range set-up image and setting up the scan range or the image producing range based on the range set-up image.

The present invention also offers:

an X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the X-ray CT device comprising:

a first scan controlling unit for performing control in such a manner that first projection data is acquired in accordance with a first image-taking condition by moving the X-ray source and the patient in a relative manner to each other along the body axis of the patient;

a range setting-up unit for displaying a scan range set-up image that is used to set up a scan range or an image producing range, based on the first projection data;

a second scan controlling unit for performing control in such a manner that second projection data is acquired in accordance with a second image-taking condition that is different from the first image-taking condition by moving the X-ray source and the patient in a relative manner to each other along the body axis of the patient;

a third scan controlling unit for performing control in such a manner that third projection data is acquired by rotating the X-ray source around the patient in accordance with the scan range or the image producing range set up by the range setting-up unit; and a reconstruction processing unit for performing a reconstruction process by combining the first projection data with the third projection data or by combining the first and second projection data with the third projection data.

According to the present invention, methods of imposing limitations on the conditions of collecting line data and managing data are established so that an X-ray CT device which prevents image reconstruction from being based on erroneous data, as well as a method of controlling such a device, can be realized.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The embodiments of the present invention will be explained below with reference to the attached drawings.

EMBODIMENT 1

Figure 1:
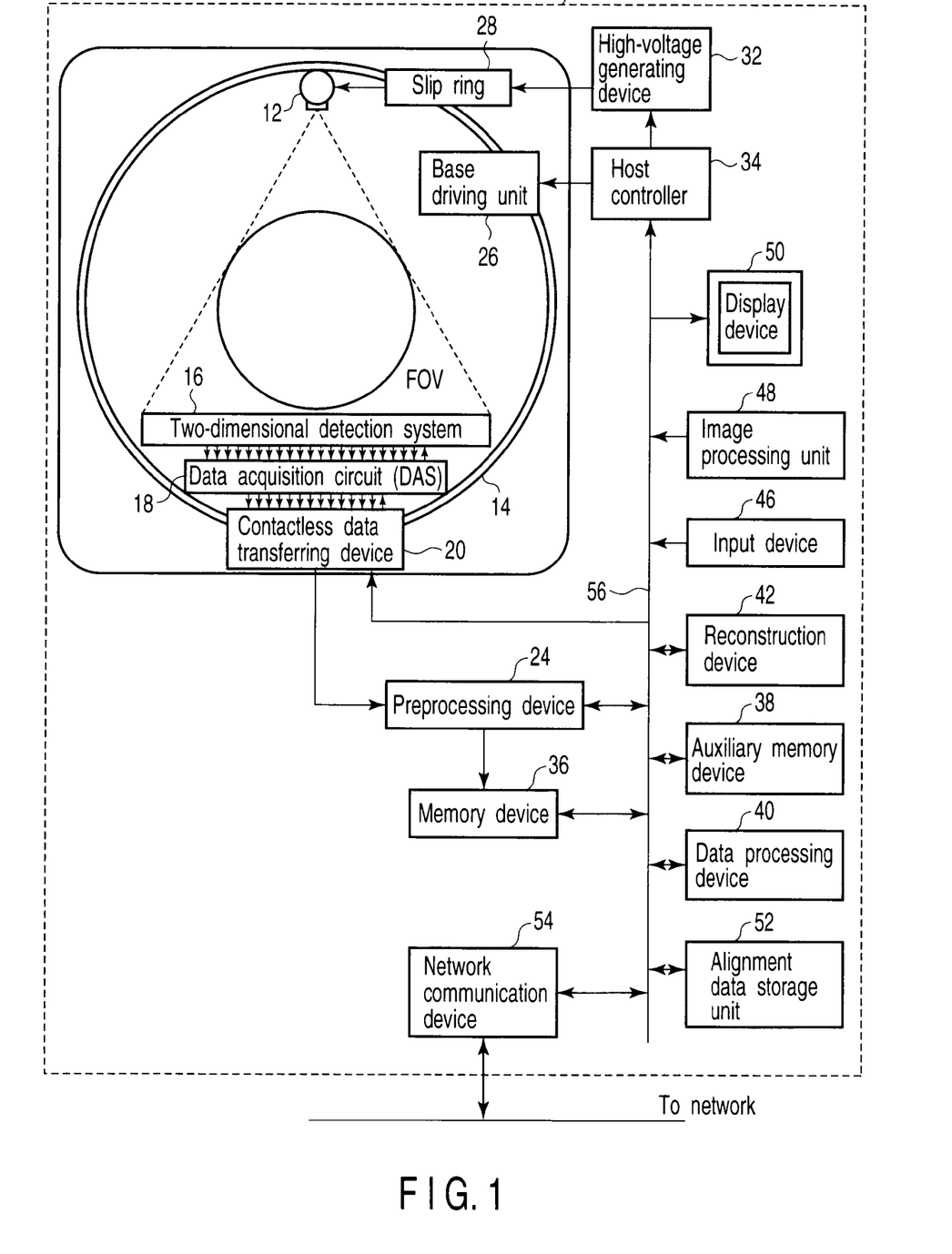
FIG. 1 is a block diagram showing a structure of an X-ray CT device 10 according to the first embodiment of the present invention.
Figure 2:
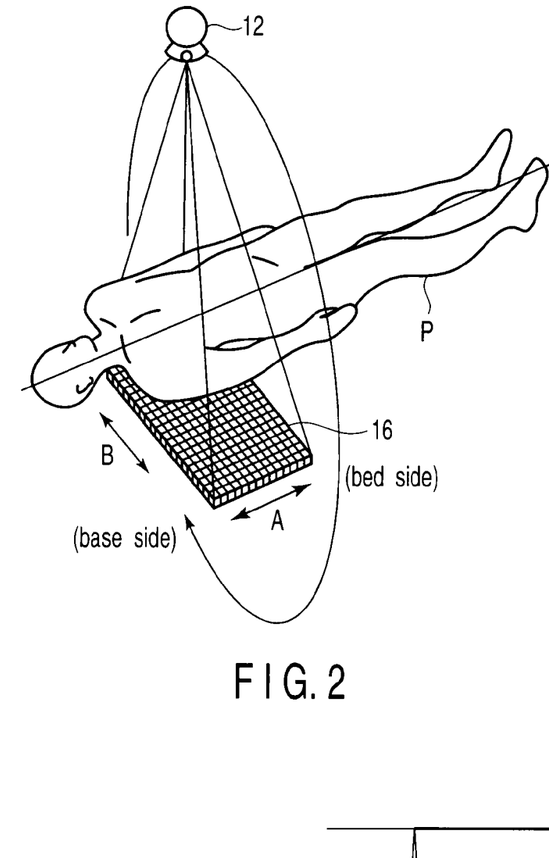
FIG. 2 is a perspective view of a tomogram-taking configuration with the X-ray CT device 10 of FIG. 1.

FIG. 1 is a block diagram showing a structure of an X-ray CT device 10 according to the first embodiment of the present invention. FIG. 2 is a perspective view of a tomogram-taking configuration with the X-ray CT device 10 of FIG. 1;

X-ray CT devices can be classified into various types such as a rotate-rotate type having an X-ray tube and a detection system uniformly formed to rotate around a subject, a stationary-rotate type having detection elements arranged into the shape of a ring and only an X-ray tube configured to rotate around a subject, and a type that electronically changes the position of the X-ray source by polarizing the electron beam. The technical idea of the present invention is applicable to an X-ray CT device of any type. In other words, as long as the device incorporates an X-ray tube and a detector capable of handling a multi-slice scan, the idea of the present invention can be applied to the device.

In the following explanation, an X-ray CT device of a most-used rotate-rotate type will be discussed as an example.

As illustrated in FIG. 1, the X-ray CT device 10 comprises an X-ray tube 12, a rotation ring 14, a two-dimensional detection system 16, a data acquisition circuit (DAS) 18, a contactless data transferring device 20, a preprocessing device 24, a base driving unit 26, a slip ring 28, a high-voltage generating device 32, a host controller 34, a memory device 36, an auxiliary memory device 38, a data processing device 40, a reconstruction device 42, an input device 46, an image processing unit 48, a display device 50, an alignment data storage unit 52, a network communication device 54, and a data-control bus 56. In addition, an external image processing device (not shown in the drawing) is connected to the main body of the device 10 by way of the data-control bus 56.

The X-ray tube 12 is an X-ray source that is arranged on the rotation ring 14 to produce X-ray beams. The high-voltage generating device 32 supplies power necessary for X-ray projection to the X-ray tube 12 via the slip ring 28. The X-ray tube 12 uses the supplied high voltage to accelerate electrons and collide them with the target. A cone-shaped X-ray beam is thereby projected onto a subject P positioned in an effective field of view FOV.

In addition, it is preferable, in order to realize the image taking with high precision, that the relative position of the X-ray tube 12 be adjusted with respect to the two-dimensional detection system 16 in such a manner that the center of the X-ray beam corresponds to the center of the two-dimensional detection system 16 at the time of image taking.

Figure 3:
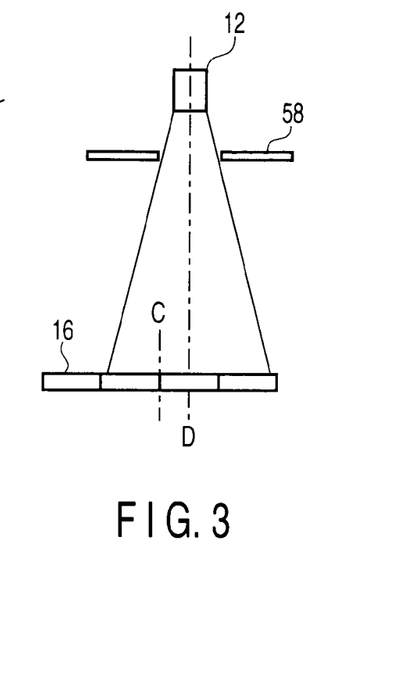
FIG. 3 is a perspective view of X-ray irradiation from an X-ray tube 12 onto a two-dimensional detection system 16.

The X-ray beam incident from the X-ray tube 12 is collimated by an upper slit 48 as illustrated in FIG. 3. If the central axis D of the X-ray beam is misaligned from the center line C of the two-dimensional detection system, the beam 16 may not be effectively projected on the detection element arrays, preventing a tomographic image from being suitably taken. Thus, it is essential that the central axis D of the X-ray beam is aligned with the center line C of the two-dimensional detection system 16.

The rotation ring 14 is provided with the X-ray tube 12, the two-dimensional detection system 16, and the data acquisition circuit 18 thereon. The rotation ring 14 is driven by the base driving unit 26, thereby rotating around the subject P together with the X-ray tube 12 and the two-dimensional detection system 16, at a high speed of one second or less per rotation.

The two-dimensional detection system 16 is a detection system for detecting X-rays that pass through the subject P. The two-dimensional detection system 16 is arranged on the rotation ring 14 in such a manner as to oppose the X-ray tube 12. As indicated in FIG. 2, the two-dimensional detection system 16 has multiple detection elements arranged two-dimensionally along the body axis of the subject P (row-wise indicated as A in the drawing) and channel-wise (indicated as B) perpendicular to the row. These detection elements are composed of combinations of scintillators and photodiodes. Approximately 1000 detection elements (1000 channels) are arranged channel-wise. (Hereinafter, a string of 1000 detection elements is referred to as a "detection element string".)

The X-ray CT device 10 is, for example, a 256-multi-slice CT device (which acquires 256 tomographs at the same time. A multi-slice CT device may include 64, 128, or 256 detection element strings). Line-circle reconstruction according to the present invention is effective especially in the situation where the cone angle of the X-ray beam is widened with a large width of the detector in the slicing direction. For instance, the present invention is useful in an X-ray CT device having 64 rows or more of detection element strings.

Furthermore, in order to realize image taking with high precision, the relative position of the two-dimensional detection system 16 is adjusted with respect to the X-ray tube 12 by using an alignment method, which will be discussed later.

The data acquisition circuit (DAS) 18 has multiple DAS chips, and a large amount of data from all the M×N channels of the two-dimensional detection system 16 (hereinafter, the data equivalent to the M×N channels in one view is referred to as "projection data") is input therein. The data is subjected to amplification and digitization processes at the data acquisition circuit 18, and then all the data is transferred at a time to the data processing unit provided on the stationary side via the contactless data transferring device 20 using optical communications.

The contactless data transferring device 20 optically transfers the acquired data of the passed through X-rays to the next downstream device. The contactless data transferring device 20 and the data acquisition circuit 18 are configured to perform ultra high-speed processes so that two-dimensional projection data that are voluminously and rapidly produced by the two-dimensional detection system 16 can be transferred without delay.

In particular, the X-rays that have passed through the subject are converted into analog electric signals by the two-dimensional detection system 16, and then converted to two-dimensional projection data incorporating digital electric signals by the data acquisition circuit 18. The converted data is sent to the preprocessing device 24, where various corrections are made.

The preprocessing device 24 receives the two-dimensional projection data from the contactless data transferring device 20 and preprocesses the data to correct the sensitivity, X-ray intensity, and the like. The preprocessed two-dimensional projection data is sent to the data processing device 40 immediately after the preprocessing, or sent thereto after it is temporarily stored in the memory device 36. According to the present embodiment, the projection data is stored after the preprocessing, but it may be stored before the preprocessing.

The base driving unit 26 executes drive control in such a manner, for example, that the X-ray tube 12 and the two-dimensional detection system 16 uniformly rotate around the central axis which is parallel to the body axis of the subject inserted into the diagnosis opening. The base driving unit 26 may perform control in such a manner that only the X-ray tube 12 rotates around the central axis.

The high-voltage generating device 32 supplies a high voltage necessary for X-ray projection to the X-ray tube 12 by way of the slip ring 28. The device 32 includes a high voltage transformer, a filament heater-transformer, a rectifier, a high voltage switch, and the like. The high voltage supply from the high-voltage generating device 32 to the X-ray tube 12 is conducted by the slip ring 28.

The host controller 34 performs centralized control over various processes including the image taking, the data processing, and the image processing. For instance, the host controller 34 stores scan conditions that are input in advance, such as a slice thickness, in the internal memory during the image taking process. Then, the process described below is executed on the basis of a scan condition automatically selected in accordance with a patient ID or the like (or a scan condition set up directly from the input device 46 in a manual mode). The host controller 34 controls the high-voltage generating device 32, the bed driving unit that is not shown in the drawing, the base driving unit 26, the amount and speed of transporting the bed along the body axis, the rotation speed and pitch of the X-ray tube 12 and the two-dimensional detection system 16, the X-ray incident timing, and the like. Then, the host controller 34 performs the X-ray CT image taking process by applying cone-shaped X-ray beams to a target image-taking field of the subject P from different directions.

The host controller 34 also performs switching control of switches of the two-dimensional detection system 16 in accordance with the scan condition. That is, the host controller 34 switches between the connection states of the detection elements of the two-dimensional detection system 16 to the data acquisition elements, and organizes the X-ray transmission data detected by the detection elements into predetermined units. Then, the host controller 34 sends the X-ray transmission data of different slices acquired in accordance with the scan condition, to the data acquisition circuit 18 that is positioned downstream to perform a predetermined process.

The auxiliary memory device 38 is provided with a high-capacity memory area in which reconstructed image data generated by the reconstruction device 42 can be stored.

The data processing device 40 includes a computer circuit having a CPU or the like and stores projection data acquired by the two-dimensional detection system 16. The data processing device 40 is configured to execute a process of adding all the projection data items for a certain slice that is acquired from different directions during the rotation of the image taking system (the X-ray tube 12 and the two-dimensional detection system 16). The data processing device 40 also performs interpolating and correcting processes, if necessary, onto the multi-directional data obtained from the adding process.

The reconstruction device 42 performs a reconstruction process onto the projection data that has been processed by the data processing device 40 to generate reconstructed image data for predetermined slices. More specifically, the reconstruction device 42 reconstructs the image data by using a two- or three-dimensional image reconstruction algorithm, typified by Feldkamp method. As a result, two-dimensional distribution data of X-ray absorption coefficients for each section crossing the body axis, or three dimensional distribution data of X-ray absorption coefficients in a target field (volume) that expands along the body axis (three-dimensional volume data of voxels that is referred to as "voxel volume data") is reconstructed. The process executed by the reconstruction device 42 is called real-time reconstruction, in which a tomographic image is reconstructed from the multi-directional projection image in a shorter time than the time required for acquiring projection data from multiple directions to reconstruct one tomographic image.

The input device 46 includes a keyboard, various switches, a mouse, and the like, which are not shown in the drawing. An operator inputs various scanning conditions such as a slice thickness and the number of slices from this input device 46.

The image processing unit 48 performs image display processing, such as window conversion and RGB processing, onto the reconstructed image data generated by the reconstruction device 42, and outputs the data to the display device 50. In response to an instruction from the operator, the image processing unit 48 also generates pseudo three-dimensional images such as a tomographic image of a designated section, a projection image from a designated direction and a three-dimensional surface image, and outputs a generated image on the display device 50. The image data output from the image processing unit 48 is displayed as an X-ray CT image on the display device 50.

The network communication device 54 exchanges information with other devices having a communicating function via a network such as an in-house LAN and the Internet. The network communication device 54 transmits and receives especially image information and maintenance information of the X-ray CT device 10 via the Internet or the like.

It is common that the data processing such as reconstruction and section conversion and the computation processing for displaying operations are executed within the X-ray CT device 10. However, the processing may be executed by an external image processing device such as a workstation. It should be noted that the effects of the present invention would not be influenced by the data that is transmitted from the X-ray CT device 10 to the external image processing device in any state, whether it is transmitted before or after the reconstruction or immediately before the display following the data processing.

In the X-ray CT device 10, a scanogram is often obtained in advance for scan planning. Thus, when the line-circle reconstruction method is adopted, a scanogram is first acquired, and then projection data on the linear track (hereinafter referred to as linear track data) is acquired by linear track scan, while projection data on the circular track (hereinafter referred to as circular track data) is acquired by circular track scan. Thereafter, a reconstructed image without artifacts is formed on the basis of the two types of data. Instead of the linear track data, helical track data may be acquired by helical track scan and combined with the circular track data to perform the reconstruction process.

Figure 4A:
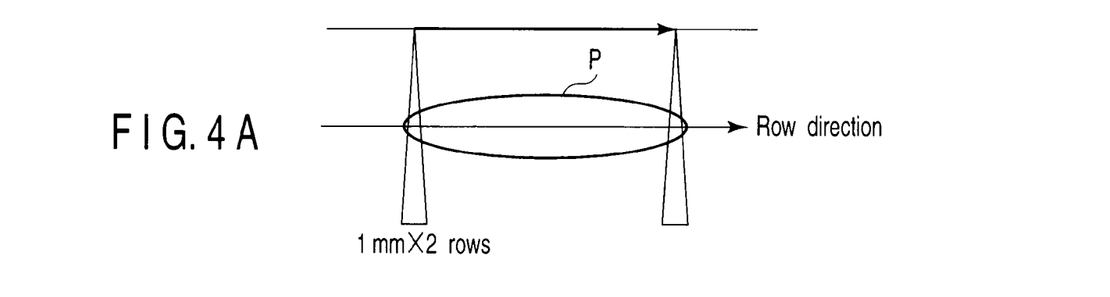
FIG. 4A is a diagram for explaining a method of acquiring data by use of a scanogram on the X-ray CT device according to the first embodiment of the present invention.
Figure 4B:
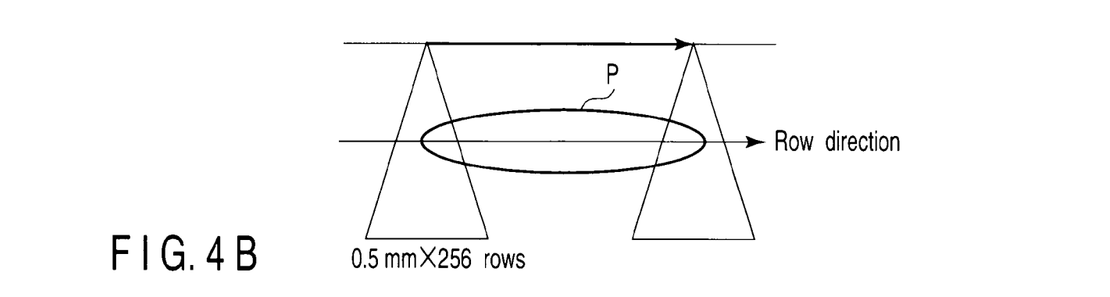
FIG. 4B is a diagram for explaining a method of acquiring linear track data on the device.

The scanogram data may be acquired by two 1-millimeter detection element strings at small cone angles as illustrated in FIG. 4A. On the other hand, a greater cone angle with 256 0.5-millimeter detection element strings is required to acquire linear track data, as illustrated in FIG. 4B. However, the scanogram acquisition and linear data acquisition have a commonality that data is collected with the base being kept still. This means that, if the scan protocol is fixed such as in a routine examination, linear data can be collected in place of a scanogram so that the linear data of the center and nearby rows can be used for a scanogram.

Now, the fundamental operations of the X-ray CT device 10 according to the present embodiment will be explained with reference to the flowchart of FIG. 5.

First, a linear track scan is performed to acquire linear track data in step S1, with X-rays projected from the X-ray tube 12. The number of rows of linear track data, the acquisition thickness, the voltage of the X-ray tube, and the tilt angle of the base that are adopted in a protocol are uniquely determined because they need to be the same as the values in the circular track scan. If the conditions of the linear track scan do not agree with those of the circular track scan predetermined as a scan plan, a warning is issued to the user to draw attention because the line-circle reconstruction cannot be executed under these conditions. The warning may be given, for example, by presenting on the display device a message that the reconstruction is not viable or by using a sound that is not shown in the drawing. Furthermore, whether the combination of the data is suitable for the reconstruction may be determined not only from the scanning conditions but also from patient identification information, information on the image taking area and image taking date and the like.

The linear track data acquired in step S1 is stored in the memory device 36. The linear track data is associated with the scanning condition when the data is stored.

Next, the acquisition range is determined in step S2. A scano-image (image used for setting up the taking range) is created from the linear track data.

For the linear track data, two-dimensional projection data is acquired from different positions by changing the taking positions. Each piece of the two-dimensional projection data is acquired in such a manner that the pieces can be superimposed with one another in the slicing direction. The scano-image is created by extracting projection data with a small cone angle in the slicing direction from the two-dimensional projection data that is acquired from different positions and overlaying the data together. In other words, the projection data acquired by the detection element strings that are positioned around the center of the slicing direction is extracted from the two-dimensional projection data taken from different positions, and the extracted pieces of the data are placed at the corresponding positions in the slicing direction so as to produce a scano-image. A marker indicating the image producing range or scanning range is displayed on the scano-image so that the ranges can be set up by moving the markers.

When the linear track data is not sufficient enough to perform reconstruction in the determined image producing range or scanning range, either a warning is issued or the process is prevented from moving onto the next step. Whether the data is sufficient or not is determined based on a judgment as to whether the linear track data is available in the range obtained in the method that will be discussed later.

Figure 6A:
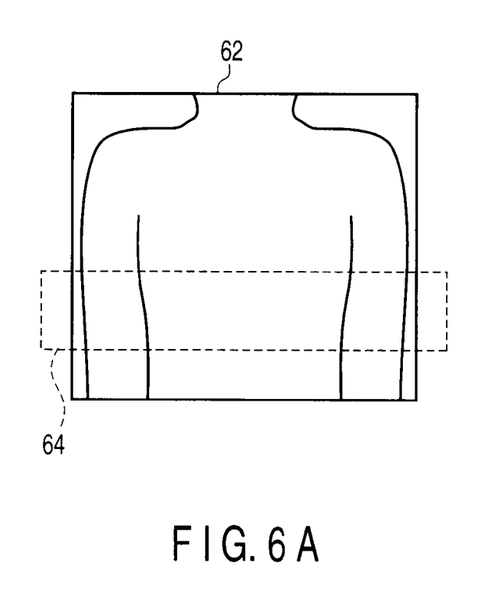
FIG. 6A is a diagram showing an example of an image taking range marker 64 displayed on a scano-image 62.
Figure 6B:
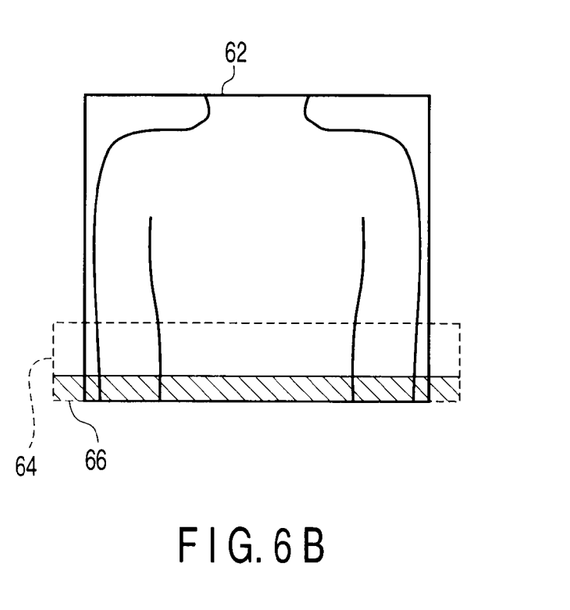
FIG. 6B is a diagram showing the image taking range marker 64 and an image production inoperable area marker 66 displayed on the scano-image 62.

An image taking range marker 64 (indicated by dashed lines) is displayed on a scano-image 62, as illustrated in FIG. 6A, to show the scanning range or the image producing range. When it is difficult to produce an excellent image due to insufficient linear track data, an image production inoperable area marker 66 (indicated by a shaded portion) is displayed on the scano-image 62 together with the marker 64, as illustrated in FIG. 6B, to show that the portion is an image production inoperable (or degradation) area.

The range for acquiring the linear track data is determined uniquely from the size and position of the reconstruction ROI. In other words, the range can be expressed as a function of calibration FOV, the tilt angle, the presence/absence of a mask on the extrapolated portion, the reconstruction range, the scanning position, and the line data acquisition direction (the position of the tube). The acquisition range is calculated by the host controller 34, the data processing device 40, or the like.

In the following explanation, it is assumed that (i) the device is not tilted and (ii) the reconstruction ROI is symmetrical with respect to the mid-plane.

First, the length W that is half the width of the detector necessary to completely cover the reconstruction ROI is defined.

$$W = (N\text{seg} + 2\text{Exp}S) \times \text{SegSize}/2 \quad (1)$$

Figure 7:
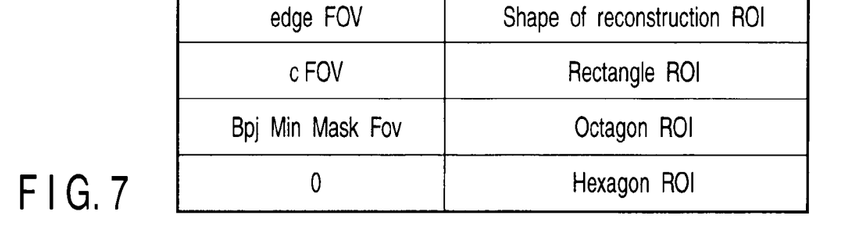
FIG. 7 is a diagram indicating the relationship between an effective field of view and the shape of a reconstruction ROI.

The row extrapolation amount (of one side) ExpS is determined by the following expressions (2) and (3) and in accordance with FIG. 7, on the basis of the shape of the calibration FOV "cFOV" and the reconstruction ROI.

$$\text{Exp}S = \text{edge}FOV \times N\text{seg} \times \text{SegSize}/(2FCD - \text{edge}FOV) \quad (2)$$

$$\text{edgeFOV} = \min[\text{cFOV}, \text{BpjMinMaskFOV}] \quad (3)$$

Figure 8A:
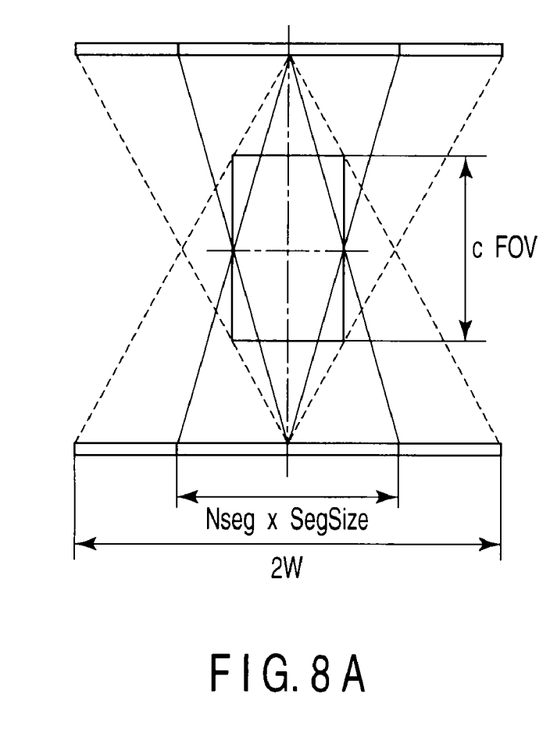
FIGS. 8A to 8C show examples of different shapes of reconstruction ROI's, with a rectangular ROI on FIG. 8A, an octagonal ROI on FIG. 8B, and a hexagonal ROI on FIG. 8C.
Figure 8B:
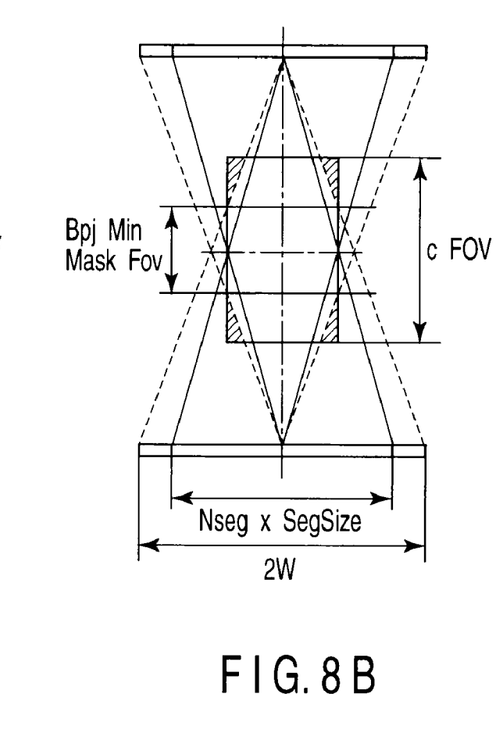
Figure 8C:
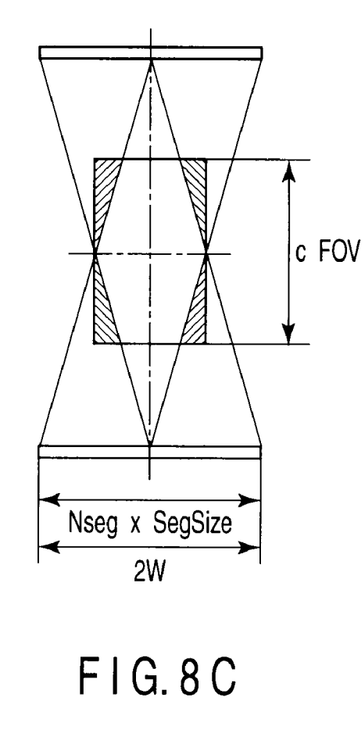

FIGS. 8A to 8C show examples of the shapes of the reconstruction ROI. FIG. 8A shows a rectangular ROI, FIG. 8B shows an octagonal ROI, and FIG. 8C shows a hexagonal ROI.

Figure 9:
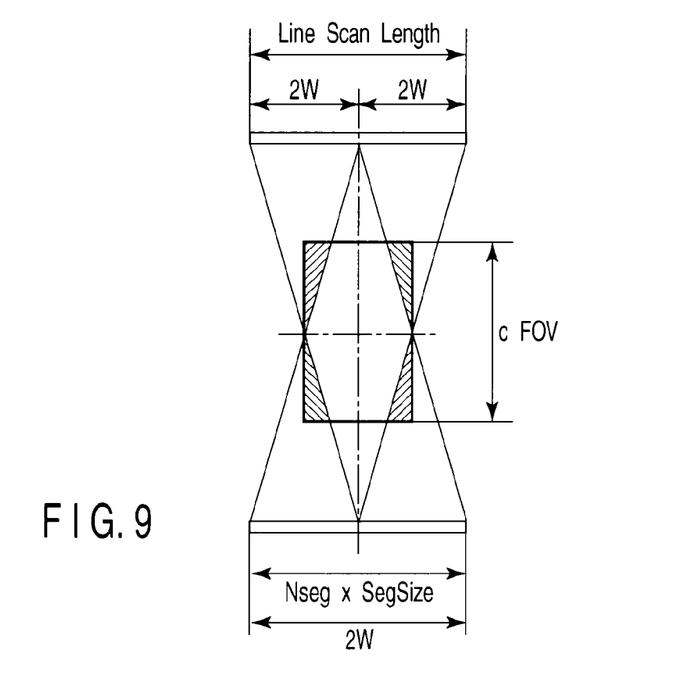
FIG. 9 is a diagram for explaining the necessary length of line data "Line Scan Length"

The necessary length of the linear track data "Line Scan Length" as illustrated in FIG. 9 can be expressed by the following expression:

$$\text{Line Scan Length} = 4W \quad (4)$$

Figure 10:
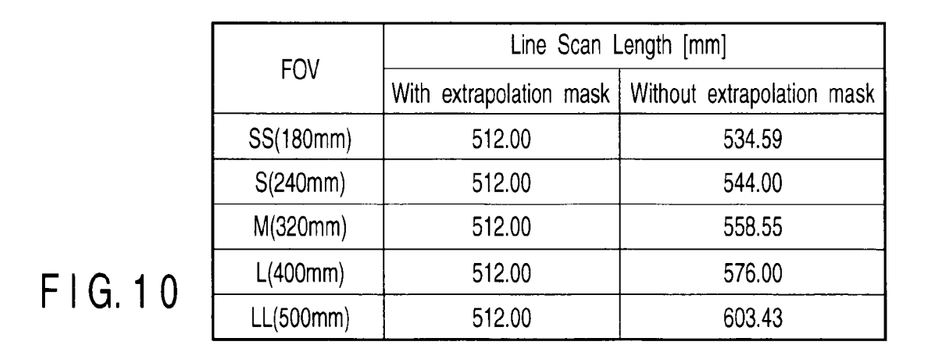
FIG. 10 is a diagram showing examples of data acquisition ranges with 0.5 mm×256 rows without a tilt.

Here, examples of data acquisition ranges are given in FIG. 10, when the acquisition is executed with 0.5 mm×256 rows and the device is not tilted.

The bed has flexibility in its direction of movement during data acquisition and may move in either the IN or OUT direction. The system should be provided with manual and automatic modes. In manual mode, the user explicitly determines the direction of moving the bed during data acquisition. This mode is useful when the user desires to acquire data in a specific direction so as to ensure the route. In automatic mode, the movement is minimized to acquire the linear track data. The direction can be automatically calculated on the basis of the end position of scanogram acquisition and the position of the circular track scan.

When the acquisition range is determined, a circular track scan is executed in accordance with this acquisition range in step S3. The circular track data acquired in step S3 is stored in the memory device 36. Here, the scanning condition is stored in association with the circular track data. Then, an image is reconstructed by the reconstruction device 42 in step S4 on the basis of the data acquired from the linear track scan in step S1 and the data acquired from the circular track scan in step S3. The image reconstruction technology is well known, and thus the details are omitted from the explanation.

After the reconstructed image is obtained, the reconstructed image is displayed on the display device 50 in step S5.

In this manner, the method according to the present embodiment can minimize the additional X-ray exposure by suitably designing the line data acquisition.

An example of the operation modified from the flowchart of FIG. 5 will be discussed with reference to the flowchart of FIG. 11.

When the sequence is initiated, a scan plan is set up in step S11. At this step, the scan plan is made to define the order and conditions of scanning. That is, the scanning conditions for the line track scan and the circular track scan, which will be discussed later, are made and compared with each other to check whether or not the combination of the scanning conditions is suitable for the reconstruction, which will also be discussed later. When the combination is found to be unsuitable as a result of the comparison, either a warning message is presented or the process is prevented from moving to the next step.

Next, the linear track scan is executed in step S12. The condition for the linear track scan may be changed here. When a change is made to the condition, the conditions for the linear track scan and for the circular track scan are compared with each other to see whether the combination is suitable for the reconstruction. When the combination is found to be unsuitable, either a warning message is presented to indicate as such or the device is prevented from performing the linear track scan, in a similar manner to step S11.

After the acquisition range is determined in step S13, the circular track scan is executed in step S14. Here, the condition for the circular track scanning may be changed. When a change is made to the condition, the conditions for the linear track scan and for the circular track scan are compared with each other to see whether the combination is suitable for the reconstruction. When the combination is found to be unsuitable, either a warning message is presented to indicate as such, or the device is prevented from performing the linear track scan.

In step S15, the reconstruction is executed. Here, the scanning condition that is associated with the linear track data and the scanning condition that is associated with the circular track data are compared with each other to see whether or not the combination is suitable for the reconstruction. If the combination is not suitable for the reconstruction, a warning message is displayed to indicate as such, or the device is prevented from performing the reconstruction process.

Finally, the reconstructed image is displayed in step S16. As mentioned before, in the case of an image reconstructed from the combination that is not suitable for the reconstruction, a warning message that the image is generated from the combination of data unsuitable for the reconstruction is presented.

Figure 5:
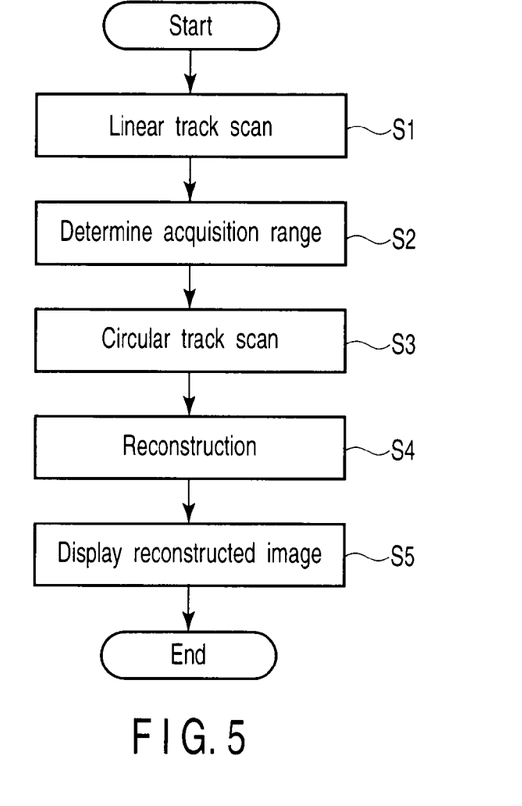
FIG. 5 is a flowchart for explaining a fundamental operation of the X-ray CT device according to the first embodiment of the present invention.
Figure 11:
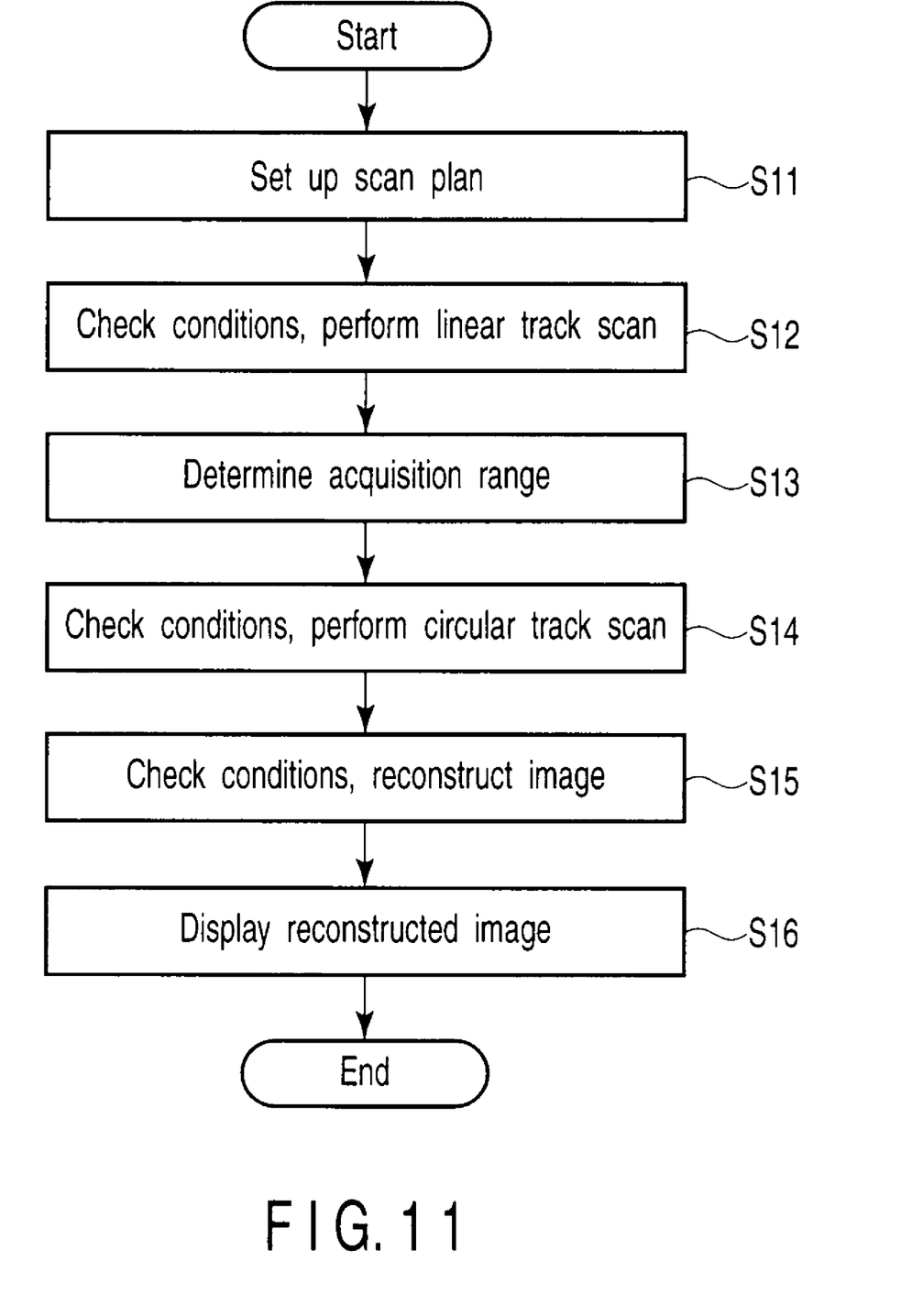
FIG. 11 is a flowchart of modified operations of the flowchart of FIG. 5.

The user may arbitrarily switch between and select the method according to the flowchart of FIG. 5 and the method according to the flowchart of FIG. 11 on the X-ray CT device 10.

As described above, linear track data is acquired in place of a scanogram, and a scanogram is created from the data near the center row of the linear track data. Such a line-circle reconstruction method can minimize additional X-ray exposure.

In the line-circle reconstruction method according to the present embodiment, the number of rows of line data, the acquisition thickness, the voltage of the X-ray tube, and the tilt angle of the base adopted for the protocol have to take on the same values as those for the circular track scan. Thus, the host controller 34 checks to see whether the conditions for the two scans match. If the conditions (such as the voltages of the X-ray tube and the tilt angles of the base) do not match, a warning is issued.

Figure 12:
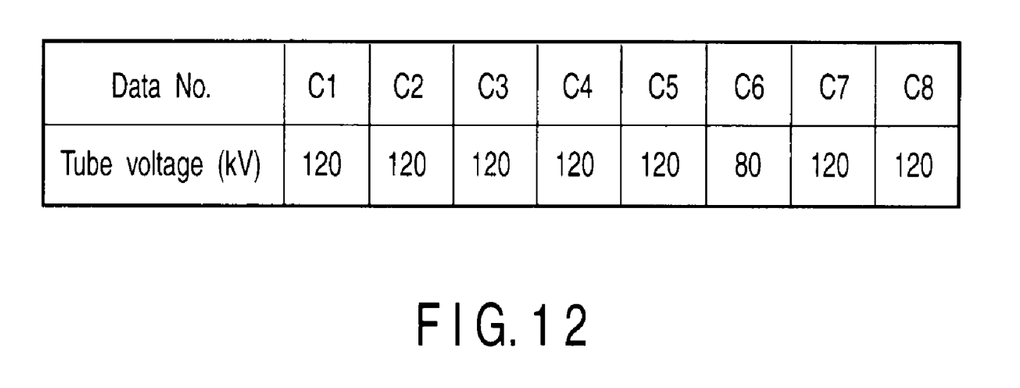
FIG. 12 is a diagram of an example data in which the conditions do not match in the line-circle reconstruction according to the first embodiment of the present invention.

For instance, when there is a tube voltage that is different from others (data C6 being 80 kV) as indicated in FIG. 12, an artifact-free image cannot be produced by the line-circle reconstruction method according to the present embodiment. For this reason, a warning may be displayed on the display device 50 to inform that the reconstructed image is not effective, or the operation may be terminated to disable the scan.

Figure 13:
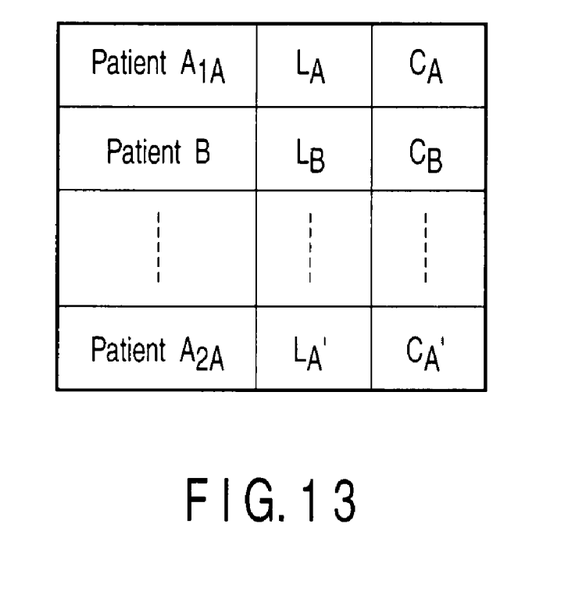
FIG. 13 is a diagram of an example data in which the conditions do not match in the line-circle reconstruction according to the first embodiment of the present invention where data for a plurality of patients are included.

Furthermore, when more than one patient is being dealt with as indicated in FIG. 13, it is certainly meaningless to combine the circular track data of patient A with the line data of patient B. Furthermore, it is equally meaningless to combine the circular track data $C_A$ with the line data $L_A'$ of the same patient but from different data acquisition dates (patient $A_{1A}$ and patient $A_{2A}$, for example) or the circular track data of the abdominal area with the line data of the chest area.

Data management is important in order to avoid the reconstruction based on any meaningless combination of data. Thus, each item of data is provided with a management tag so that the reconstruction is allowed by the host controller 34 only when the management tags of the items match.

In this manner, the system can be realized, which allows line data acquisition under suitable conditions, while prohibiting reconstruction based on data items with inconsistent conditions.

Moreover, line data acquisition conditions for the linear track scan need to match the conditions for the circular track scan, with respect to the data acquisition thickness, the number of rows of the data, the voltage of the X-ray source, the tilt angle of the base, the acquisition starting point and the acquisition length. The values may be set up by the user, or by the host controller 34 or the like so as to have the same values.

EMBODIMENT 2

According to the first embodiment, when the conditions do not agree with one another as indicated in FIG. 12, either a warning is issued or the operation is suspended. However, when the data is insufficient as the case of data C6, the structure may be configured in such a manner that the second scan is automatically executed or that any necessary operation is executed.

Alternatively, when any data item whose condition does not agree with others is included, the structure may be configured in such a manner that the reconstruction is performed without suspending the scanning operation but simply skipping the portion that includes the inconsistency, or without making any correction but making use of other data. In such a case, a warning should still be issued to inform that an accurate reconstructed image would not be attained.

Furthermore, the voltage of the X-ray tube may be set to two different values (120 kV and 80 kV, for example) to perform a linear track scan and then a circle scan. A reconstructed image may be obtained in this manner.

Figure 14:
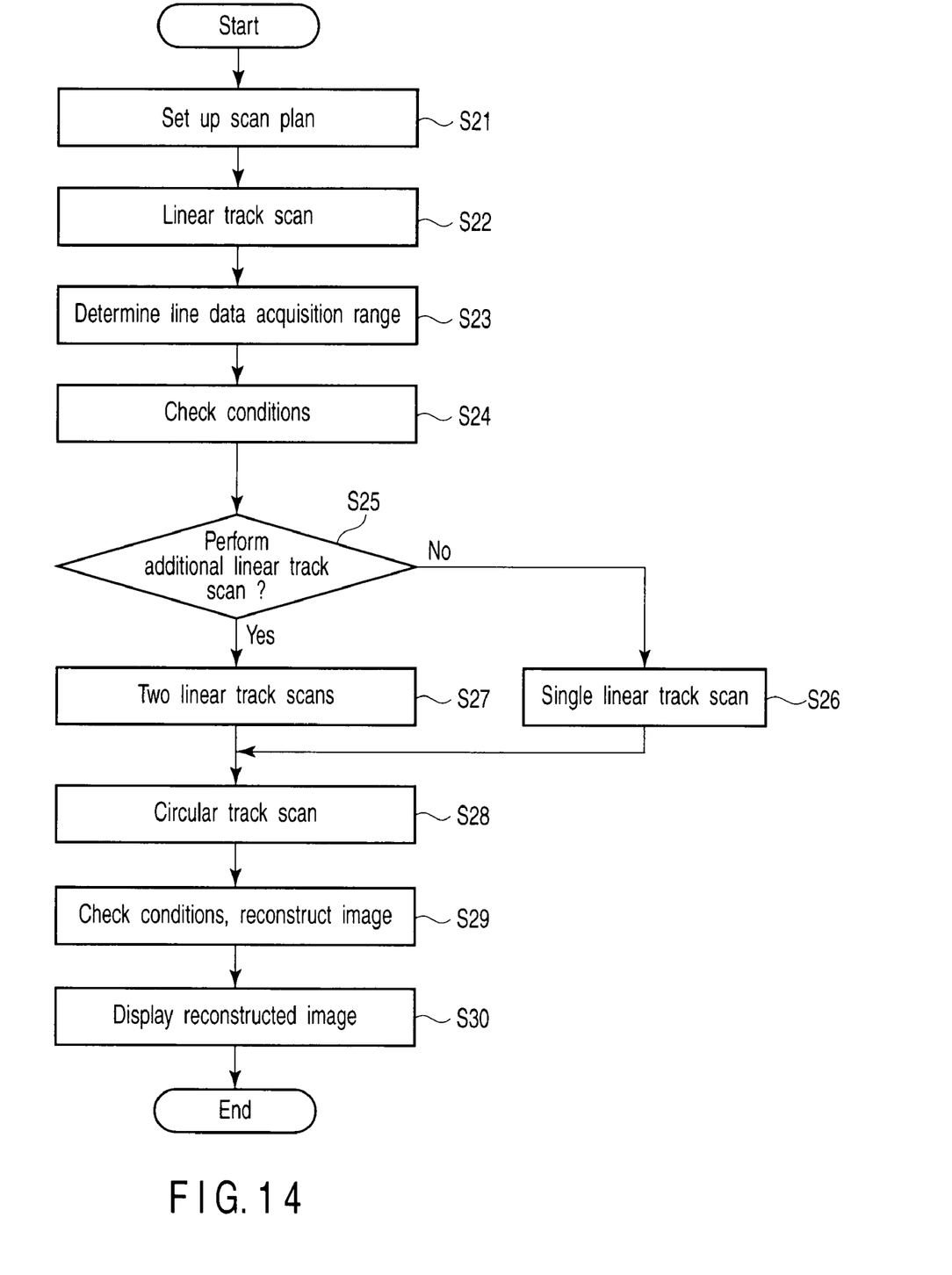
FIG. 14 is a flowchart for explaining a fundamental operation of an X-ray CT device according to the second embodiment of the present invention.

FIG. 14 is a flowchart for explaining a basic operation of an X-ray CT device according to the second embodiment of the present invention.

When the sequence is initiated, a scan plan is set up in step S21 in a similar manner to the aforementioned step S11 indicated in the flowchart of FIG. 11. It is assumed here that the linear track scan is determined to be performed only once (with the voltage of the X-ray tube being 120 kV, for instance). Then, the linear track scan is performed in step S22. When the acquisition range for the linear track scanning is determined in step S23, the scan conditions are checked in step S24. Whether the X-ray tube adopts two voltages of 80 kV and 120 kV or only one voltage of 120 kV is determined here.

Next, whether or not an additional linear track scan is performed is determined in step S25. When there is no additional scan, the process proceeds to step S26, where the linear track scan is performed only once with the tube voltage of 120 kV. In this case, data C6 indicated in FIG. 12 becomes an image with no correction added, whereas other items of data C1 to C5, C7 and C8 become images with corrections thereto.

On the other hand, when it is determined in step S25 that an additional scan is to be performed, the process proceeds to step S27, where two linear track scans are performed, with the tube voltages of 120 kV and 80 kV. More specifically, the tube voltage of 80 kV is adopted for data C6 indicated in FIG. 12, whereas the tube voltage of 120 kV is adopted for other data items.

Thereafter, the circular track scan is performed in step S28, in a similar manner to step S15 in the flowchart of FIG. 11. Then, the reconstruction is executed in step S29. If the combination is not suitable for the reconstruction, a warning is issued to indicate as such, or the reconstruction process is prevented from being executed. Finally, a reconstructed image is displayed in step S30. As discussed before, when the image is reconstructed based on the combination of data that is not suitable for the reconstruction, a warning is displayed to indicate that the image is produced from an unsuitable combination of data.

In this manner, additional X-ray exposure can be reduced even when linear track scanning is performed multiple times.

The embodiments of the present invention have been discussed above, but the present invention should not be limited to these embodiments. It should be noted that various modifications may be made without departing from the scope of the present invention.

Furthermore, the above embodiments include different steps of the invention, and thus various inventions can be attained from suitable combinations of disclosed structural elements. As long as the problems mentioned in the Brief Summary of the Invention can be solved and the aforementioned advantages can be attained, the structure may be presented as an invention even if, for instance, some of the structural elements described in the embodiments are omitted or some of the structural elements are combined together.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the X-ray CT device comprising:
    a scan controlling unit for performing control in such a manner that first projection data is acquired by moving the X-ray source and the patient in a relative manner to each other along the body axis of the patient and second projection data is acquired by rotating the X-ray source around the patient;
    a reconstruction processing unit for performing a reconstruction process by combining the first projection data and the second projection data; and
    a determining unit for determining whether a scan should be performed or whether the reconstruction process should be performed, based on a scan condition of the first projection data and a scan condition of the second projection data.

2. The X-ray CT device according to claim 1, further comprising:
    a warning unit for issuing a warning to indicate that a normal image is not allowed to be obtained from the scan or the reconstruction process, based on a determination made by the determining unit as to whether the scan should be performed or whether the reconstruction process should be performed.

3. An X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the X-ray CT device comprising:
    a first scan controlling unit for performing control in such a manner that first projection data is acquired by moving the X-ray source and the patient in a relative manner to each other along the body axis of the patient;
    a range setting-up unit for displaying a scan range set-up image that is used to set up a scan range or an image producing range, based on the first projection data;
    a second scan controlling unit for performing control in such a manner that second projection data is acquired by rotating the X-ray source around the patient in accordance with the scan range or the image producing range set up by the range setting-up unit; and
    a reconstruction processing unit for performing a reconstruction process by combining the first projection data and the second projection data.

4. A method of controlling an X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the method comprising steps of:
    acquiring first projection data by moving the X-ray source and the patient in a relative manner to each other along the body axis of the patient;
    displaying a range set-up image that is used to set up a scan range or an image producing range, based on the first projection data and thereby setting up the scan range or the image producing range;
    acquiring second projection data by rotating the X-ray source around the patient in accordance with the scan range or the image producing range set up in the preceding step; and
    performing a reconstruction process by combining the first projection data and the second projection data.

5. The method of controlling the X-ray CT device according to claim 4, further comprising a step of:
    setting up scan conditions for the first projection data and the second projection data and determining whether the combination of the scan conditions is suitable for the reconstruction process before acquiring the first projection data.

6. An X-ray CT device provided with an X-ray source that generates X-ray beams spreading along the body axis of a patient, an X-ray detecting unit in which detection elements for detecting X-rays that pass through the patient are arranged in a plurality of rows along the body axis of the patient, and a reconstructing unit for reconstructing an image from data detected by the X-ray detecting unit, the X-ray CT device comprising:
    a first scan controlling unit for performing control in such a manner that first projection data is acquired in accordance with a first image-taking condition by moving the X-ray source and the patient in a relative manner to each other along the body axis of the patient;

a range setting-up unit for displaying a scan range set-up image that is used to set up a scan range or an image producing range, based on the first projection data;

a second scan controlling unit for performing control in such a manner that second projection data is acquired in accordance with a second image-taking condition that is different from the first image-taking condition by moving the X-ray source and the patient in a relative manner to each other along the body axis of the patient;

a third scan controlling unit for performing control in such a manner that third projection data is acquired by rotating the X-ray source around the patient in accordance with the scan range or the image producing range set up by the range setting-up unit; and a reconstruction processing unit for performing a reconstruction process by combining the first projection data with the third projection data or by combining the first and second projection data with the third projection data.

7. The X-ray CT device according to claim 6, wherein:
the first image-taking condition differs from the second image-taking condition in tube voltages of the X-ray tube.

8. The X-ray CT device according to claim 6, wherein:
the reconstruction processing unit combines the projection data in accordance with the first and second image-taking conditions.

* * * * *